United States Patent
Gedet et al.

(10) Patent No.: US 10,660,638 B2
(45) Date of Patent: May 26, 2020

(54) SURGICAL SUTURE WITH SOFT CORE

(71) Applicant: Synthes USA, LLC, West Chester, PA (US)

(72) Inventors: Philippe Gedet, Nidau (CH); Beat Lechmann, Grenchen (CH); Cyril Voisard, Niederbipp (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 226 days.

(21) Appl. No.: 13/778,816

(22) Filed: Feb. 27, 2013

(65) Prior Publication Data

US 2013/0231700 A1    Sep. 5, 2013

Related U.S. Application Data

(60) Provisional application No. 61/605,730, filed on Mar. 1, 2012.

(51) Int. Cl.
*A61B 17/06* (2006.01)
*A43C 9/00* (2006.01)
(Continued)

(52) U.S. Cl.
CPC .......... *A61B 17/06166* (2013.01); *A43C 9/00* (2013.01); *A61L 17/145* (2013.01);
(Continued)

(58) Field of Classification Search
CPC .... A61B 17/06166; A61B 2017/06171; A61B 2017/06176; A61B 2017/0618;
(Continued)

(56) References Cited

U.S. PATENT DOCUMENTS 3,847,156 A * 11/1974 Trumble ..................... 606/231
3,942,532 A    3/1976 Hunter et al.
(Continued)

FOREIGN PATENT DOCUMENTS

CN    1623016    6/2005
CN    201543004    8/2010
(Continued)

OTHER PUBLICATIONS

Tongkui Cui, Yongnian Yan, Renji Zhang, Li Liu, Wei Xu, and Xiaohong Wang. "Rapid Prototyping of a Double-Layer Polyurethane-Collagen Conduit for Peripheral Nerve Regeneration". Tissue Engineering Part C: Methods. Mar. 2009, 15(1): 1-9. doi:10.1089/ten.tec.2008.0354.*
(Continued)

*Primary Examiner* — Katherine H Schwiker
(74) *Attorney, Agent, or Firm* — Morgan, Lewis & Bockius LLP

(57) ABSTRACT

A fastening element includes (a) a non-load bearing core, the non-load bearing core includes a first biocompatible polymer; and (b) a load bearing sheath, the load bearing sheath including a second biocompatible polymer, wherein the load bearing sheath surrounds the non-load bearing core. The fastening element can be used as a suture, shoe lace or rope. The non-load bearing core has a Durometer Hardness Type A value ranging from 15 to 30. The load bearing sheath is formed from a plurality of yarns, each yarn comprising a plurality of filaments in form of mono or multifilament of the second biocompatible polymer. Each yarn may have a tenacity at break value ranging from 30 cN/dtex to 45 cN/dtex.

20 Claims, 7 Drawing Sheets

(51) Int. Cl.
*D04C 1/12* (2006.01)
*A61L 17/14* (2006.01)
*A61B 17/00* (2006.01)

(52) U.S. Cl.
CPC ...... *D04C 1/12* (2013.01); *A61B 2017/00858* (2013.01); *A61B 2017/00964* (2013.01); *D10B 2509/04* (2013.01); *Y10T 24/37* (2015.01)

(58) Field of Classification Search
CPC ........... A61B 2017/06185; A61B 2017/00858; A61B 2017/00964; A61B 2017/0619; D10B 2509/04; A43C 9/00; A43C 9/02; A43C 9/04; A43C 9/06; A43C 9/08; D04C 1/12; Y10T 24/37; D07B 1/00; D07B 1/005; D07B 1/02; D07B 1/025; D07B 1/04; D07B 1/06; D07B 1/0606; D07B 1/0613; D07B 1/062; D07B 1/0626; D07B 1/0633; D07B 1/064; D07B 1/0646; D07B 1/0653; D07B 1/066; D07B 1/0666; D07B 1/0673; D07B 1/068; D07B 1/0686; D07B 1/0693; D07B 1/08; D07B 1/10; D07B 1/12; D07B 1/14
USPC .................................................. 606/228–231
See application file for complete search history.

(56) References Cited

U.S. PATENT DOCUMENTS

| | | |
|---|---|---|
| 4,033,603 A | 7/1977 | Horn |
| 4,209,859 A | 7/1980 | Hoffman |
| 4,461,298 A | 7/1984 | Shalaby et al. |
| 4,621,638 A | 11/1986 | Silvestrini |
| 4,662,886 A | 5/1987 | Moorse et al. |
| 4,857,602 A | 8/1989 | Casey et al. |
| 4,946,467 A * | 8/1990 | Ohi ................. A61B 17/06166 606/228 |
| 4,959,069 A | 9/1990 | Brennan et al. |
| 4,990,158 A | 2/1991 | Kaplan et al. |
| 5,102,420 A | 4/1992 | Hunter et al. |
| 5,133,738 A | 7/1992 | Korthoff et al. |
| 5,147,400 A | 9/1992 | Kaplan et al. |
| 5,217,495 A | 6/1993 | Kaplan et al. |
| 5,234,006 A | 8/1993 | Eaton et al. |
| 5,314,446 A | 5/1994 | Hunter et al. |
| 5,464,424 A | 11/1995 | O'Donnell, Jr. |
| 5,562,736 A | 10/1996 | Ray et al. |
| 5,651,377 A | 7/1997 | O'Donnell, Jr. |
| 5,810,851 A | 9/1998 | Yoon |
| 5,952,232 A | 9/1999 | Rothman |
| 6,022,376 A | 2/2000 | Assell |
| 6,045,571 A | 4/2000 | Hill |
| 6,090,117 A | 7/2000 | Shimizu |
| 6,174,333 B1 | 1/2001 | Kadiyala et al. |
| 6,197,043 B1 | 3/2001 | Davidson |
| 6,251,137 B1 | 6/2001 | Andrews et al. |
| 6,296,659 B1 | 10/2001 | Foerster |
| 6,605,294 B2 | 8/2003 | Sawhney |
| 7,175,632 B2 | 2/2007 | Singhatat et al. |
| 7,175,635 B2 | 2/2007 | Singhatat et al. |
| 7,270,666 B2 | 9/2007 | Lombardo et al. |
| 7,285,124 B2 | 10/2007 | Foerster |
| 7,329,271 B2 | 2/2008 | Koyfman et al. |
| 7,338,492 B2 | 3/2008 | Singhatat et al. |
| 7,357,810 B2 * | 4/2008 | Koyfman ........... A61B 17/0401 606/228 |
| 7,431,725 B2 | 10/2008 | Stack et al. |
| 7,469,526 B2 | 12/2008 | Patrick et al. |
| 7,674,271 B2 | 3/2010 | Bjerken |
| 7,678,138 B2 | 3/2010 | Fitts et al. |
| 7,762,287 B2 | 7/2010 | Liao |
| 7,829,485 B2 | 11/2010 | Mikura |
| 7,955,539 B2 | 6/2011 | Patel et al. |
| 8,118,834 B1 | 2/2012 | Goraltchouk et al. |
| 8,128,656 B2 | 3/2012 | Cichocki |
| 8,870,915 B2 | 10/2014 | Mayer et al. |
| 2002/0029066 A1 | 9/2002 | Foerster |
| 2004/0267313 A1 | 12/2004 | Amery et al. |
| 2005/0125035 A1 * | 6/2005 | Cichocki, Jr. ................. 606/222 |
| 2005/0130540 A1 * | 6/2005 | Crane .................... D01D 5/082 442/364 |
| 2005/0149118 A1 * | 7/2005 | Koyfman ........... A61B 17/0401 606/228 |
| 2005/0149119 A1 * | 7/2005 | Koyfman et al. ............. 606/228 |
| 2005/0247320 A1 | 11/2005 | Stack et al. |
| 2005/0267528 A1 | 12/2005 | Ginn |
| 2005/0277985 A1 * | 12/2005 | Wert ................ A61B 17/06166 606/228 |
| 2006/0025818 A1 * | 2/2006 | Ferguson ............... A61L 17/145 606/228 |
| 2006/0030883 A1 | 2/2006 | Cichocki |
| 2006/0121274 A1 | 6/2006 | Capurro |
| 2006/0155328 A1 * | 7/2006 | Foerster ........... A61B 17/06166 606/228 |
| 2006/0253126 A1 | 11/2006 | Bjerken et al. |
| 2006/0253127 A1 | 11/2006 | Bjerken |
| 2007/0005110 A1 | 1/2007 | Collier et al. |
| 2007/0060932 A1 | 3/2007 | Stack et al. |
| 2007/0118151 A1 | 5/2007 | Davidson |
| 2007/0134305 A1 | 6/2007 | Zilberman |
| 2007/0260279 A1 | 11/2007 | Hotter et al. |
| 2007/0276432 A1 | 11/2007 | Stack et al. |
| 2008/0065122 A1 | 3/2008 | Stack et al. |
| 2008/0082113 A1 | 4/2008 | Bishop et al. |
| 2008/0154266 A1 | 6/2008 | Protopsaltis et al. |
| 2008/0183272 A1 | 7/2008 | Wood et al. |
| 2008/0281355 A1 * | 11/2008 | Mayer et al. ................. 606/228 |
| 2009/0024151 A1 | 1/2009 | Shalaby et al. |
| 2009/0024162 A1 | 1/2009 | Shalaby et al. |
| 2009/0035572 A1 | 2/2009 | Hotter et al. |
| 2009/0104243 A1 * | 4/2009 | Utkhede ............... A61F 9/0017 424/423 |
| 2010/0030261 A1 * | 2/2010 | McClain ................ A61L 17/005 606/230 |
| 2010/0241146 A1 | 9/2010 | Stack et al. |
| 2011/0054524 A1 | 3/2011 | Beevers et al. |
| 2011/0197564 A1 * | 8/2011 | Zachariades ............... B32B 5/26 57/210 |
| 2011/0274824 A1 * | 11/2011 | Mazzocca ........ A61B 17/06166 427/2.31 |
| 2013/0197574 A1 | 8/2013 | Mayer et al. |
| 2013/0226234 A1 * | 8/2013 | Avelar ............. A61B 17/06166 606/231 |
| 2013/0261662 A1 | 10/2013 | Mayer et al. |

FOREIGN PATENT DOCUMENTS

| | | |
|---|---|---|
| CN | 104155479 | 11/2014 |
| EP | 0328401 | 8/1989 |
| EP | 1199036 | 4/2002 |
| EP | 1543782 | 6/2005 |
| JP | 48-23753 | 3/1973 |
| JP | 59-34264 | 2/1984 |
| JP | 63-75194 | 4/1988 |
| JP | 1-138447 | 9/1989 |
| JP | 10-500319 | 1/1998 |
| JP | 2000-125855 | 5/2000 |
| JP | 2003-19196 | 1/2003 |
| JP | 2003-265169 | 9/2003 |
| JP | 2005-177499 | 7/2005 |
| JP | 2005-520066 | 7/2005 |
| JP | 2006-515783 | 6/2006 |
| JP | 2007-515212 | 6/2007 |
| JP | 2008-539842 | 11/2008 |
| WO | 96/03084 | 2/1996 |
| WO | 98/22155 | 5/1998 |
| WO | 03/078705 | 9/2003 |
| WO | 2004/066847 | 8/2004 |
| WO | 2005/055836 | 6/2005 |
| WO | 2006/117398 | 11/2006 |

(56) References Cited

FOREIGN PATENT DOCUMENTS

| WO | 2010/052005 | | 5/2010 |
|---|---|---|---|
| WO | WO 2010052005 | A1 * | 5/2010 |
| WO | 2013/130547 | | 9/2013 |

OTHER PUBLICATIONS

Muffly et al., "Minimum Number of Throws Needed for Knot Security," Journal of Surgical Education, vol. 68, No. 2, Mar./Apr. 2011, pp. 130-133.
Brochure for ORTHOCORD Suture, DePuy Mitek, Inc., 2004.
Written Opinion of the International Searching Authority for International Application No. PCT/US2013/027943, dated May 14, 2013, 6 pages.
International Search Report for International Application No. PCT/US2013/027943, dated May 14, 2013, 5 pages.
International Preliminary Report on Patentability for International Application No. PCT/US2013/027943, dated Sep. 2, 2014, 7 pages.
D'Aversa et al. "Tensile Mechanical Property Evaluation of Two Absrobable Sutures: Effects of Size and Types," [online], [retrieved on Jul. 15, 2015]. Retrieved from the Internet <URL: http://2015.biomaterials.org/sites/default/files/abstracts/310.pdf>.
Ind et al. "Influence of training on reliability of surgical knots," British Journal of Obstetrics and Gynaecology, Oct. 2001, vol. 108, pp. 1013-1016.
Winkler et al. "Effect of suture material on tensile strength and complication rate in abdominal fascial defects repaired with acellular dermal matrix," Hernia, Feb. 2008, vol. 12, Issue 1, pp. 33-38.
Mufily et al. "Tensile strength of a surgeon's or a square knot," J Surg Educ. Author manuscript (PMCID: PMC4167833), published as J Surg Educ. 2010, vol. 67, No. 4, pp. 222-226.
Garvin et al., "Novel System for Engineering Bioartificial Tendons and Application of Mechanical Load", Tissue Engineering, Oct. 2003, 9(5), 967-979.
Harris et al., "Fibroblast Traction As A Mechanism for Collagen Morphogenesis," Nature, 290, Mar. 1981, pp. 249-251.
Cui et al, "Rapid Prototyping of a Double-Layer Polyurethane-Collagen Conduit for Peripheral Nerve Regeneration," Tissue Engineering Part C, vol. 15, No. 1., Oct. 2008, pp. 1-9.
Examination Report No. 1 dated Feb. 14, 2017 for Australian Patent Application No. 2013226225, 3 pages.
Examination Report No. 1 dated Oct. 26, 2018 for Australian Patent Application No. 2018201043, 3 pages.
Translation of First Office Action for Chinese Patent Application No. 201380011991, 4 pages.
Translation of Second Office Action for Chinese Patent Application No. 201380011991, 5 pages.
Translation of Third Office Action for Chinese Patent Application No. 201380011991, 3 pages.
Translation of Fourth Office Action for Chinese Patent Application No. 201380011991, 5 pages.
Translation of Decision of Rejection for Chinese Patent Application No. 201380011991, 7 pages.
Requisition by the Examiner dated Dec. 13, 2018 for Canadian Patent Application No. 2,865,790, pages.
Communication from European Patent Office dated Aug. 16, 2016 for European Patent Application No. 13710185, 4 pages.
Communication from European Patent Office dated May 3, 2017 for European Patent Application No. 13710185, 4 pages.
Communication from European Patent Office dated Nov. 28, 2017 for European Patent Application No. 13710185, 4 pages.
Translation of Notification of Reasons for Refusal dated Sep. 16, 2016 for Japanese Patent Application No. 2014-559963, 4 pages.
Translation of Notification of Reasons for Refusal dated Jan. 30, 2017 for Japanese Patent Application No. 2014-559963, 6 pages.
Translation of Office Action for Taiwan Patent Application No. 102107014, 5 pages.
Translation of Notice of Reexamination for Chinese Patent Application No. 201380011991, 9 pages.
Requisition by the Examiner dated Sep. 24, 2019 for Canadian Patent Application No. 2,865,790, 4 pages.
Examination Report dated Jan. 9, 2020 for Indian Patent Application No. 6720/DELNP/2014, 7 pages.

* cited by examiner

SURGICAL SUTURE WITH SOFT CORE

CROSS-REFERENCE TO RELATED APPLICATION

This application claims the benefit of U.S. Provisional Patent Application No. 61/605,730, filed Mar. 1, 2012, entitled "Surgical Suture With Soft Core", which is hereby incorporated by reference in its entirety.

FIELD OF THE INVENTION

The present disclosure is directed, at least in part, to a suture, the suture comprising a non-load bearing core and a load bearing sheath surrounding the non-load bearing core. The suture of the present invention exhibits superior knot tying and knot security properties.

BACKGROUND OF THE INVENTION

There are many circumstances in which sutures are used to repair tissue, attach tissue to a correct anatomical position or to close a wound. In many instances, a suture loop is closed by multiple knots. To prevent slippage of the suture, multiple knots, 7 or 8 knots, must be made one after the other. This results in a large number of knots which is time consuming for the surgeon. It can also result in a large mass of suture material which can cause irritations and inflammation or injure the cartilage layer of a joint. Accordingly, in an aspect, the present invention provides a braided suture with superior knot-tying characteristics.

BRIEF SUMMARY OF THE INVENTION

In accordance with an aspect of the present invention, there is provided a fastening element comprising a non-load bearing core and a load bearing sheath surrounding the non-load bearing core. In one such embodiment, the fastening element is a suture.

In some embodiments, a fastening element or suture includes a non-load bearing core; and a load bearing sheath, wherein the load bearing sheath surrounds the non-load bearing core, wherein the fastening element or suture has a tensile strength value ranging from 100 N to 400 N, and wherein the fastening element or suture has a diameter which is deformable upon application of a radial deformation force such that the diameter may be reduced by up to 40%.

In some embodiments, the suture comprises a non-load bearing core and a load bearing sheath surrounding the non-load bearing core, wherein the suture has an improved knot slippage number when tied with at least six knots compared to a suture comprising a load bearing core surrounded by a load bearing sheath.

In some embodiments, the non-load bearing core includes a first biocompatible polymer and the load bearing sheath includes a second biocompatible polymer.

In some embodiments, the load bearing sheath is in the form of braiding.

In one embodiment the non-load bearing core comprises a first biocompatible polymer. In another embodiment, the non-load bearing core has a Durometer Hardness Type A value ranging from 15 to 30. In yet another embodiment, the non-load bearing core has a tensile strength ranging from 5 MPa to 20 MPa. In another embodiment, the non-load bearing core comprises a first biocompatible polymer, wherein the first biocompatible polymer is selected from the group consisting of polysilicone, polyurethane, polyethylene glycol, polyester, collagen, alignate or chitosan. In another embodiment, the non-load bearing core comprises an osmotically active substance incorporated into the first biocompatible polymer.

In another exemplary embodiment of the fastening element or suture of the present invention, the load bearing sheath comprises a second biocompatible polymer. In an embodiment, the second biocompatible polymer comprises a polyolefin. In one embodiment, the polyolefin is a polyethylene. In yet another embodiment, the second biocompatible polymer comprises a polyolefin having a weight average molecular weight ranging from 500,000 g/mole to 5,000,000 gram/mole.

In another exemplary embodiment of the fastening element or suture of the present invention, the load bearing sheath is formed from a plurality of yarns, each yarn in the form of mono or multifilament of the second biocompatible polymer. In yet another embodiment, the plurality of yarns are braided to form a sheath or a braiding. In some embodiments, each yarn has a tenacity at break value ranging from: 30 cN/dtex to 45 cN/dtex;

In some embodiment, the fastening element or suture of the present invention has a tensile strength value ranging from 100 N to 400 N. In another embodiment, the fastening element or suture has a diameter which is deformable upon application of a radial deformation force such that the diameter is reduced by up to 40%.

In another embodiment, the present invention provides for a method to reduce knot slippage of a suture using the various suture embodiments described herein.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

DETAILED DESCRIPTION OF THE INVENTION

Figure 1A:
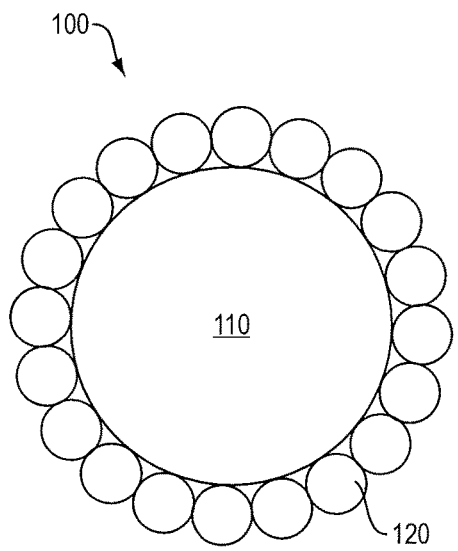
FIG. 1A illustrates a cross-sectional view of an exemplary suture of the present invention.

In some embodiments, the present invention provides for a fastening element comprising (a) a non-load bearing core, the non-load bearing core comprising a first biocompatible polymer; (b) a load bearing sheath, the load bearing sheath comprising a second biocompatible polymer, wherein the load bearing sheath surrounds the non-load bearing core. In such embodiments, the fastening element can be used as a suture, shoe lace or rope.

In some embodiments, the present invention provides for suture comprising a non-load bearing core comprising a first biocompatible polymer; a load bearing sheath comprised of a second biocompatible polymer, wherein the load bearing sheath surrounds the non-load bearing core, wherein the suture has a tensile strength value ranging from 100 N to 400 N, and wherein the suture has a diameter which is deformable upon application of a radial deformation force. In some embodiments, the suture diameter is deformed in a uniform manner. In some such embodiments, the suture is deformed into a circular shape having a diameter less than the original suture diameter. In some such embodiments, the suture diameter is reduced by up to 40%. In some other such embodiments, the suture diameter is reduced by 5% to 40%. In some other embodiments, the suture is deformed in a non-uniform manner. In some such embodiments, the suture is deformed into an elliptical shape. In some such embodiments, the suture diameter is reduced by up to 40%. In some other such embodiments, the suture diameter is reduced by 5% to 40%.

Various embodiments of the non-load bearing core, load bearing sheath are discussed below. Each of the embodiments may be used for embodiments of the fastening element as a suture, shoe lace and/or rope.

A. A Non-Load Bearing Core

Hardness of a wide variety of materials, including rubber, plastics, elastomers, foams and polymer materials may be determined using Durometers. There are several scales of durometer, used for materials with different properties. ASTM D2240-00 testing standard calls for a total of 12 scales, depending on the intended use: types A, B, C, D, DO, E, M, O, OO, OOO, OOO-S, and R. Each scale results in a value between 0 and 100, with higher values indicating a harder material. The A scale is usually used for softer plastics, while the D scale is used for harder plastics.

In an exemplary embodiment of the present invention, the non-load bearing core has a Durometer Hardness Type A value ranging from 15 to 30. In another embodiment, the non-load bearing core has a Durometer Hardness Type A value ranging from: 15 to 30, from 16 to 30, from 17 to 30, from 18 to 30, from 19 to 30, from 20 to 30, from 21 to 30, from 22 to 30, from 23 to 30, from 24 to 30, from 25 to 30, from 26 to 30, from 27 to 30, from 28 to 30, and from 29 to 30. In another embodiment, the non-load bearing core has a Durometer Hardness Type A value which is: at least 15; at least 20; at least 25; or at least 30.

In an embodiment the present invention, the non-load bearding core has a tensile strength ranging from 5 MPa to 20 MPa. In another embodiment, the non-load bearding core has a tensile strength in the range of: 5 MPa to 20 MPa, from 6 MPa to 20 MPa, from 7 MPa to 20 MPa, from 8 MPa to 20 MPa, from 9 MPa to 20 MPa, from 10 MPa to 20 MPa, from 11 MPa to 20 MPa, from 12 MPa to 20 MPa, from 13 MPa to 20 MPa, from 14 MPa to 20 MPa, from 15 MPa to 20 MPa, from 16 MPa to 20 MPa, from 17 MPa to 20 MPa, from 18 MPa to 20 MPa, and from 19 MPa to 20 MPa.

The non-load bearing core of the present invention can be composed of any suitable biocompatible material. In an exemplary embodiment, the non-load bearing core comprises a first biocompatible polymer, the first biocompatible polymer being selected from the group consisting of polysilicone, polyurethane, polyethylene glycol, polyester, collagen, alignate, chitosan and combinations thereof.

In other embodiments, the non-load bearing core includes an osmotically active substance incorporated into the first biocompatible polymer. In some such embodiments, the osmotically active substance includes biocompatible inorganic salts, superabsorbent polymers (SAP) also called slush powder and aqueous solutions thereof. In some such embodiments, the inorganic salts include sodium chloride, calcium chloride, calcium carbonate, tricalcium phosphate or mixtures thereof. In other embodiments, the osmotically active substance includes organic, osmotically active molecules such as low-molecular-weight polysaccharides including dextran and superabsorbent polymers. In some such embodiments, the superabsorbent polymer may include poly-acrylic acid sodium salt (sometimes referred to as sodium polyacrylate), polyacrylamide copolymer, ethylene maleic anhydride copolymer, cross-linked carboxymethyl-cellulose, polyvinyl alcohol copolymers, cross-linked polyethylene oxide, and starch grafted copolymer of polyacrylonitrile. In some embodiments, the osmotically active substances can also be embedded within the non-load bearing core so to improve handling and to further influence the kinetics of osmosis.

B. A Load Bearing Sheath

In an exemplary embodiment, the load bearing sheath of the present invention comprises a second biocompatible polymer. In other embodiments, the load bearing sheath is formed from a plurality of yarns, each yarn in the form of mono or multifilament of the second biocompatible polymer.

In some embodiments, the second biocompatible polymer comprises a polyolefin. In another embodiment, the polyolefin is polyethylene. In one embodiment, the polyethylene has a weight average molecular weight ranging from 500,000 g/mole to 5,000,000 gram/mole. In another embodiment, the polyethylene has a weight average molecular weight ranging from 1,000,000 g/mole to 5,000,000 gram/mole.

In some embodiments, the load bearing sheath is formed from a plurality of yarns. In some such embodiments, each yarn has a tenacity at break value ranging from: 30 cN/dtex to 45 cN/dtex; or 35 cN/dtex to 45 cN/dtex. In some other such embodiments, each yarn has a tenacity at break value of up to 45 cN/dtex. In some embodiments, each yarn may have a dtex value ranging from: 25-450 and contain 20-800 filaments. In some other embodiments, each yarn may have a dtex value ranging from: 55-165 and contain 20-300 filaments. In some other embodiments, each yarn may have a dtex value of 110 and contain 200 filaments.

In some embodiments, the plurality of yarns are braided to form the load bearing sheath. In some such embodiments, the number of yarns included in the braid range from 10 to 32. In some other such embodiments, the number of yarns included in the braid range from 10 to 20. In some yet other such embodiments, the number of yarns included in the braid range from 15 to 20. In some embodiments, the braid can have a pick count per inch ranging from 60 to 90 pic counts per inch.

D. Suture Characteristics and Method of Use

The suture, of the present invention, can be characterized by a variety of physical properties. In one embodiment, the suture has a tensile strength value ranging from: 100 N to 400 N; 250 N to 400 N; or 300 N to 400 N. In some embodiments, the suture diameter is deformed in a uniform manner upon application of a radial deformation force. In some such embodiments, the suture is deformed into a circular shape having a diameter less than the original suture diameter. In some such embodiments, the suture diameter is reduced by up to 40%. In some other such embodiments, the suture diameter is reduced by 5% to 40%. In some other embodiments, the suture is deformed in a non-uniform manner upon application of a radial deformation force. In some such embodiments, the suture is deformed into an elliptical shape. In some such embodiments, the suture diameter is reduced by up to 40%. In some other such embodiments, the suture diameter is reduced by 5% to 40%.

A need exists for sutures capable of forming surgical knots that are as small as possible by reducing the number and close to the joints to prevent excessive tissue reaction when absorbable sutures are used, or to minimize foreign body reaction to non-absorbable sutures. Also, a suture can form a knot whose ends could be cut as short as possible without the risk of slippage and/or the knot becoming untied advantageously minimize irritations and inflammations or and/or injury to surrounding tissue (cartilage layer of a joint, for example). The suture of the present invention is particularly useful for this purpose as illustrated in the examples.

The suture of the present invention address one or more of these needs by having superior knot tying and knot security properties, permitting surgeons to execute accurate surgical wound closures more rapidly (by tying fewer knots, for example) with minimal risk the knots slipping or becoming untied, while also minimizing and/or preventing hemorrhage and exogenous microbial infections. In particular, the sutures may be used for applications involving fixation of soft tissue to bone, soft tissue to soft tissue or holding soft tissue in approximation.

While not wishing to be bound by theory, it is the non-load bearing core of the present suture acts as a "soft core" takes none or a very small part of the load when the suture is in use whilst the braid takes the majority of the load. Thus, when a surgeon ties knots in the suture to block the suture (i.e. prevent the knots from untying or loosening), the soft core collapses and/or becomes squashed. As a result the knots have an increased contact area at the crossing points, which has a net effect of increasing the friction in the knot. This in turn allows the surgeon to block sutures with minimal number of knots (with as few as two or three knots in some cases).

The suture, of the present invention, has improved knot tying properties and may be used in methods to reduce knot slippage. In some embodiments, the suture comprises a non-load bearing core and a load bearing sheath surrounding the non-load bearing core, wherein the suture has an improved knot slippage number when tied with at least six knots compared to a suture comprising a load bearing core surrounded by a load bearing sheath.

E. Figures

Figure 1B:
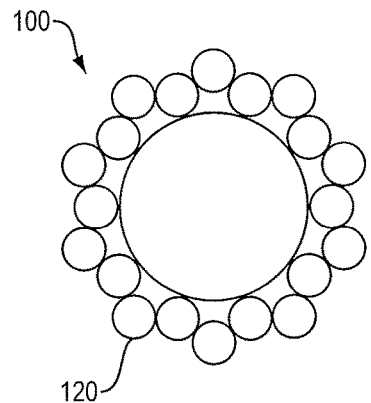
FIG. 1B illustrates a cross-sectional view of an exemplary suture of the present invention.
Figure 1C:
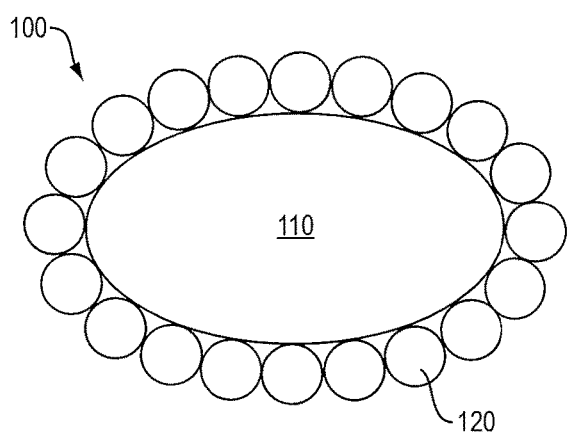
FIG. 1C illustrates a cross-sectional view of an exemplary suture of the present invention.
Figure 1D:
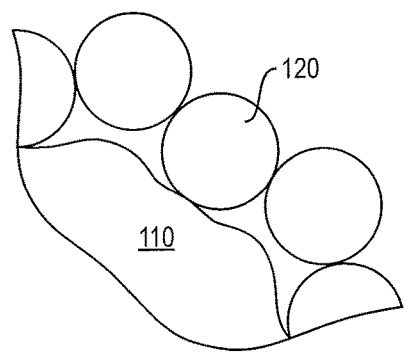
FIG. 1D illustrates a cross-sectional view of an exemplary suture of the present invention.

FIGS. 1A-1D illustrate four cross-sectional views of exemplary sutures 100 of the present invention. In FIG. 1A, the non-load bearing core 110 is surrounded by a load bearing sheath made of 20 braided yarns 120. In FIG. 1B, the non-load bearing core 110 is surrounded by a load bearing sheath made of 20 braided yarns wherein the suture has been deformed in a uniform manner to reduce the suture diameter. In FIG. 1C, the non-load bearing core 110 is surrounded by a load bearing sheath made of 20 braided yarns wherein the suture has been deformed to an elliptical shape. In FIG. 1D, the non-load bearing core 110 is surrounded by a load bearing sheath made of 20 braided yarns wherein the suture has been deformed in a non-uniform manner in the radial direction to reduce the diameter by up to 40%.

Figure 2:
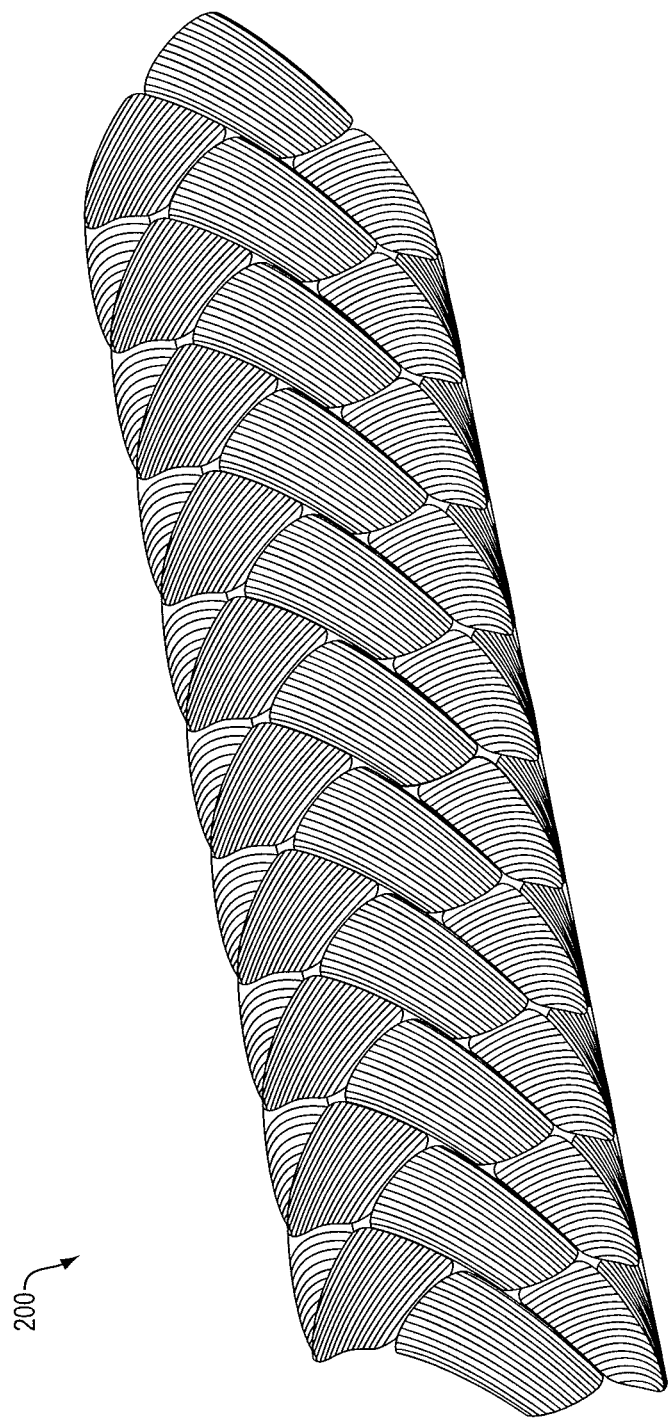
FIG. 2 illustrates an exemplary suture having a braided load bearing sheath of the present invention.

FIG. 2 illustrates an exemplary suture 200 of the present invention showing the load bearing sheath in a braided structure.

Figure 3:
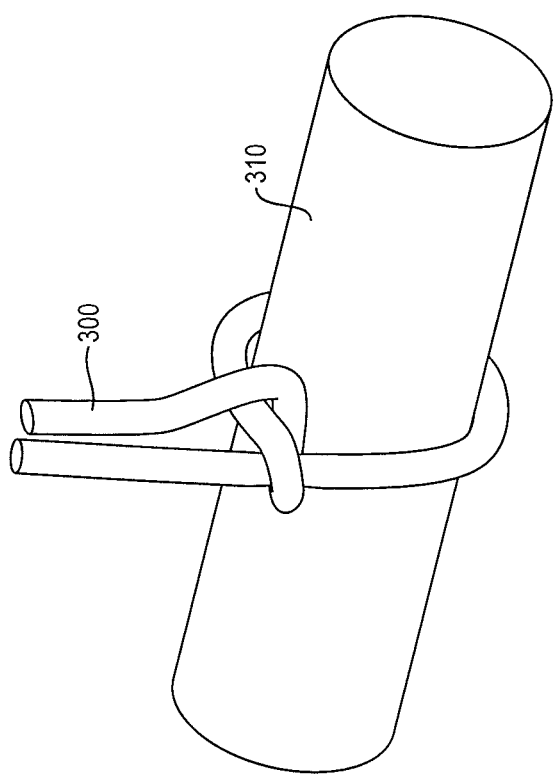
FIG. 3 illustrates the tying of an exemplary suture of the present invention.

FIG. 3 illustrates an exemplary suture 300 of the present invention being tied about an object 310.

EXAMPLES

Figure 4:
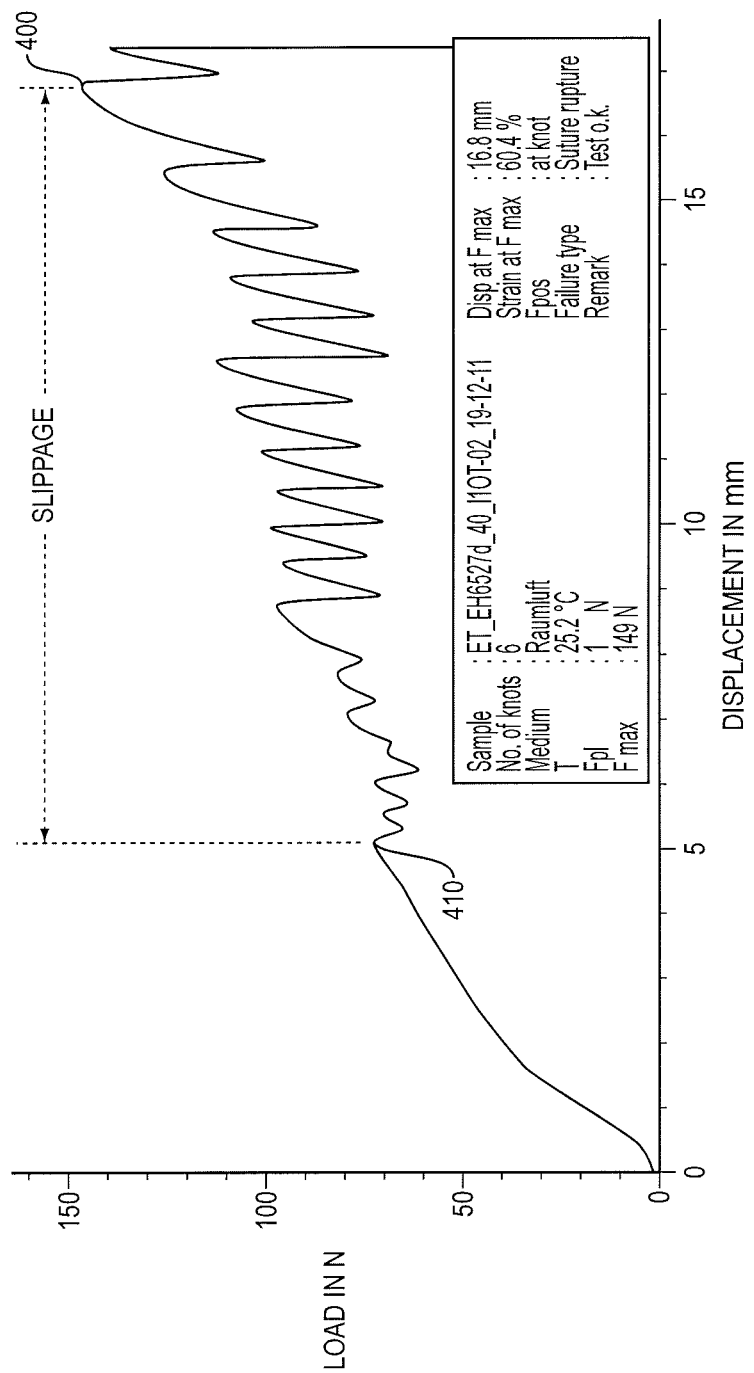
FIG. 4 illustrates knot slippage, determined by displacement versus applied tensile load, for prior art suture with six knots.

Prior Art Yarn: The knot slippage number of a prior art Polyester braided suture for a loop of six knots, for example, a six throw square knot, was determined by measuring displacement versus tensile load. For the purposes of this application knot slippage is defined as [(Displacement at maximum force−Displacement for the last distance of no knot slippage)÷(Displacement at maximum force)]×100. In FIG. 4, the Displacement at maximum force occurred at 16.8 mm (400), the Displacement for the last distance of no knot slippage occurred at 5.1 mm (410) for a knot slippage number of 69.64%.

Figure 5:
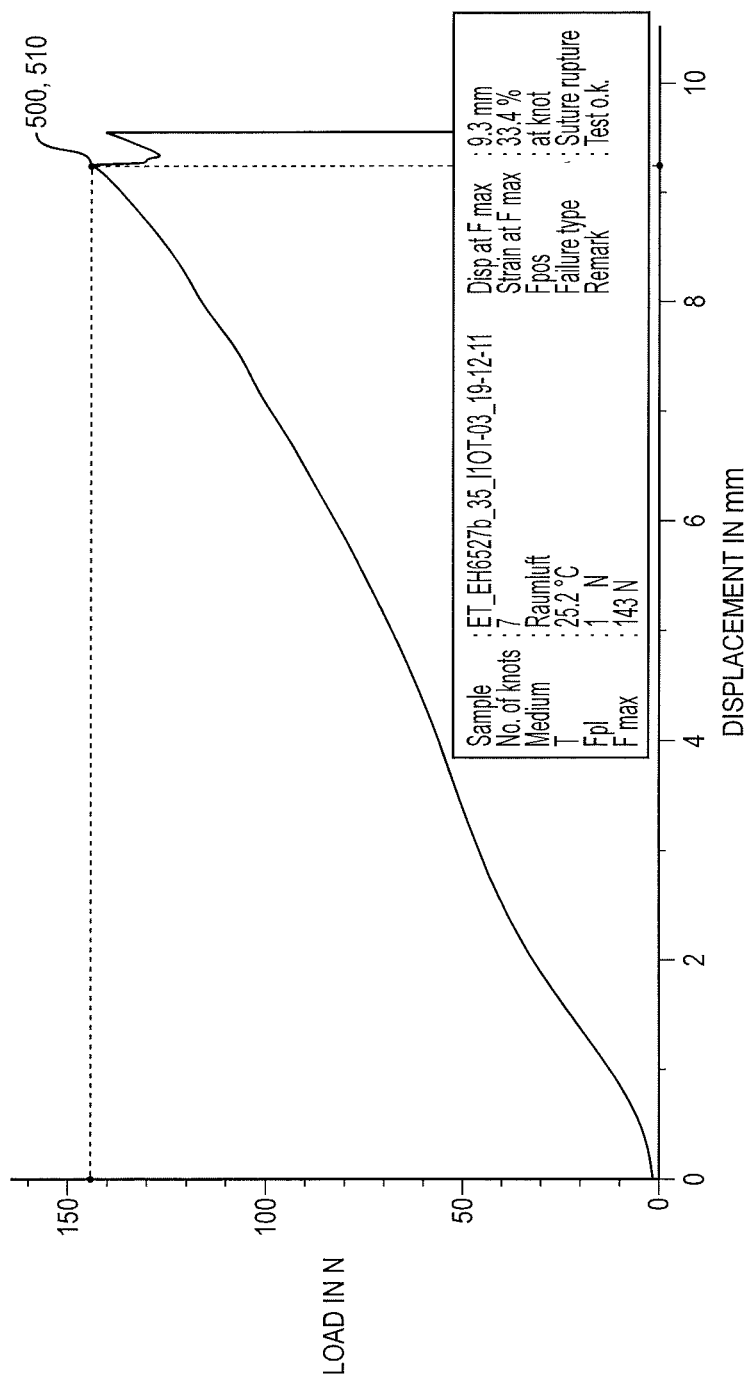
FIG. 5 illustrates knot slippage, determined by displacement versus applied tensile load, prior art suture with seven knots.

The knot slippage numbers of a loop made of seven knots, for example, a seven throw square knot, using the same suture as in FIG. 4 was measured as described above. In FIG. 5, the Displacement at maximum force occurred at 9.3 mm (500), the Displacement for the last distance of no knot slippage occurred at 9.3 mm (510) for a knot slippage number of 0%.

Figure 7:
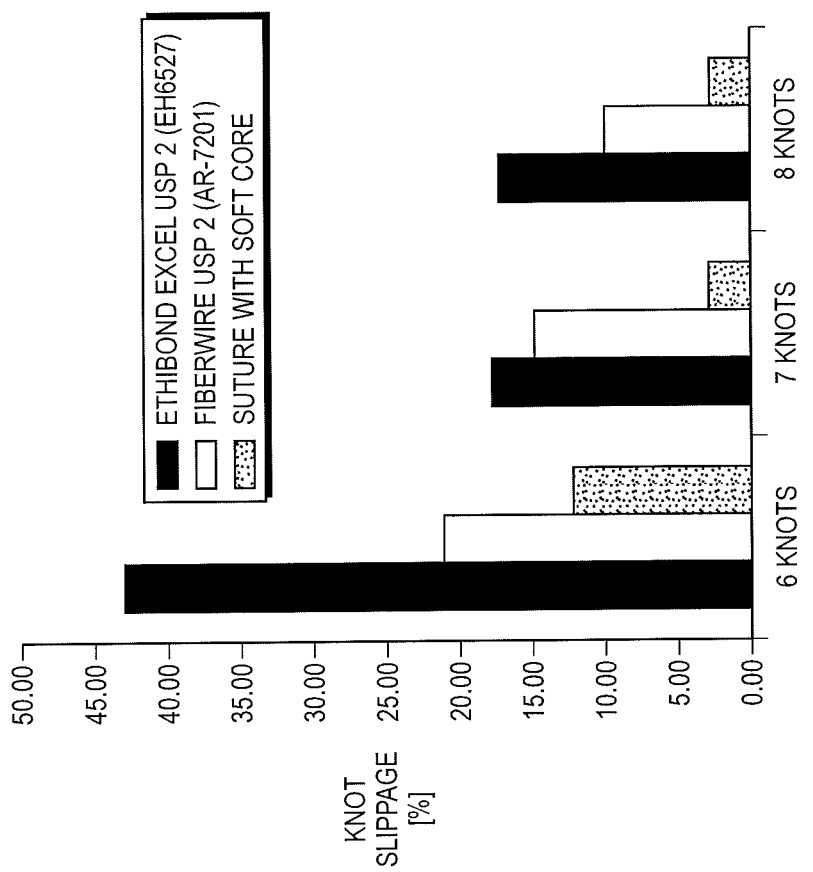
FIG. 7 illustrates a bar graph showing the knot slippage of an exemplary suture of the present invention compared to prior art sutures.

The knot slippage numbers for two prior art sutures (Ethibond & FiberWire) was measured as described above. The data is illustrated graphically in the bar graph of FIG. 7 and tabulated in Table 1.

Figure 6:
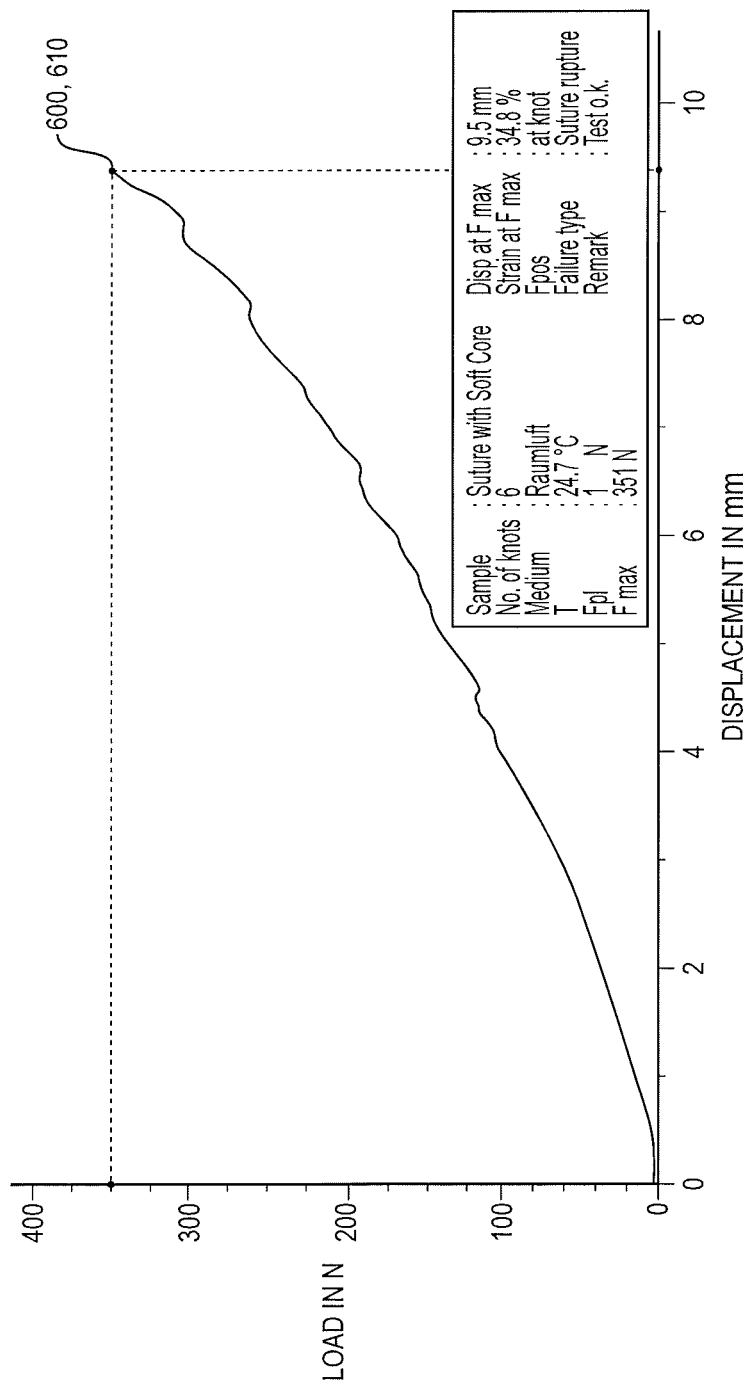
FIG. 6 illustrates knot slippage of exemplary suture of the present invention with six knots.

Inventive Example: The knot slippage numbers of a loop made of six knots, for example, a six throw square knot, using an exemplary suture of the present invention was measured as described above. In FIG. 6, the Displacement at maximum force occurred at 9.5 mm (600), the Displacement for the last distance of no knot slippage occurred at 9.5 mm (610) for a knot slippage number of 0%.

The knot slippage numbers for an exemplary suture of the present invention (Suture with Soft Core) was measured as described above. The data is illustrated graphically in the bar graph of FIG. 7 and tabulated in Table 1. When used to tie six (6) knots, the three sutures, for prior art suture and the exemplary suture, illustrated knot slippage numbers ranging from 12.32% to 42.98%. However, when used to tie seven or eight knots, the exemplary sutures of the present invention illustrated reduced knot slippage numbers, 3.03% to 3.16%, compared to the knots made using prior art sutures, 10.18% to 17.88%.

TABLE 1

|  | 6 Knots, % | 7 Knots, % | 8 Knots, % |
| --- | --- | --- | --- |
| Prior Art: Ethibond Excel USP 2 (EH6527) | 42.98 | 17.88 | 17.45 |
| Prior Art: FiberWire USP 2 (AR-7201) | 21.19 | 15.15 | 10.18 |
| Exemplary Suture with Soft Core | 12.32 | 3.03 | 3.16 |

It should be understood that various changes, substitutions, and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

The invention claimed is:

1. A fastening element configured to be tied into one or more knots, the fastening element comprising:
   a non-load bearing core comprising a first biocompatible polymer and having a tensile strength ranging from 5 MPa to 20 MPa and a Durometer Hardness Type A value ranging from 15 to 30; and
   a load bearing sheath comprising a second biocompatible polymer,
   wherein the load bearing sheath surrounds the non-load bearing core, wherein the non-load bearing core is configured to collapse when the fastening element is tied into the one or more knots, wherein the non-load bearing core has a radius that is larger than a thickness of the load bearing sheath when the non-load bearing core is not collapsed, and wherein the fastening element has a tensile strength value ranging from 100 N to 400 N.

2. The fastening element of claim 1, wherein the first biocompatible polymer is selected from a group consisting of: polysilicone, polyurethane, polyethylene glycol, polyester, collagen, alignate or chitosan.

3. The fastening element of claim 1, wherein the load bearing sheath has a braid structure.

4. The fastening element of claim 1 wherein the load bearing sheath is formed from a plurality of yarns, each yarn of the plurality of yarns comprising a plurality of filaments in a form of mono or multifilaments of the second biocompatible polymer.

5. The fastening element of claim 4, wherein each yarn of the plurality of yarns has a tenacity at break value ranging from 30 cN/dtex to 45 cN/dtex.

6. The fastening element of claim 4, wherein the plurality of yarns of the second biocompatible polymer are braided to form the load bearing sheath.

7. The fastening element of claim 1, wherein the second biocompatible polymer comprises a polyolefin.

8. The fastening element of claim 7, wherein the polyolefin is polyethylene having a weight average molecular weight ranging from 500,000 g/mole to 5,000,000 gram/mole.

9. The fastening element of claim 1, wherein the fastening element has a diameter which is deformable upon application of a radial deformation force such that the diameter is reducible by up to 40%.

10. The fastening element of claim 1, wherein the non-load bearing core comprises an osmotically active substance incorporated into the first biocompatible polymer.

11. The fastening element of claim 10, wherein the osmotically active substance is an inorganic salt independently selected from a group consisting of: sodium chloride, calcium chloride, calcium carbonate, tricalcium phosphate or mixtures thereof.

12. The fastening element of claim 1, wherein the fastening element is a suture.

13. The fastening element of claim 1, wherein the fastening element is a shoe lace.

14. The fastening element of claim 1, wherein the fastening element is a rope.

15. The fastening element of claim 1, wherein the first biocompatible polymer is selected from a group consisting of: polysilicone, polyurethane, and polyethylene glycol.

16. The fastening element of claim 1, wherein the first biocompatible polymer is selected from a group consisting of: collagen, alginate, and chitosan.

17. The fastening element of claim 1, wherein the non-load bearing core comprises a superabsorbent polymer.

18. A suture configured to be tied into one or more knots, the suture comprising:
    a non-load bearing core comprising a first biocompatible polymer and having a tensile strength ranging from 5 MPa to 20 MPa and a Durometer Hardness Type A value ranging from 15 to 30; and
    a load bearing sheath comprising a second biocompatible polymer, wherein the load bearing sheath surrounds the non-load bearing core,
    wherein the non-load bearing core is configured to collapse when the suture is tied into the one or more knots, wherein the non-load bearing core has a radius that is larger than a thickness of the load bearing sheath when the non-load bearing core is not collapsed, wherein the suture has a tensile strength value ranging from 100 N to 400 N, and wherein the suture has a diameter which is deformable, upon application of a radial deformation force, such that the suture diameter is reducible by up to 40%.

19. The suture of claim 18, wherein the suture has a knot slippage number of 3.03% to 3.16% when tied with seven or eight knots.

20. A suturing method comprising the steps of:
    providing a suture according to claim 18; and
    tying the suture into one or more knots, wherein tying the suture into one or more knots causes the non-load bearing core to collapse.

* * * * *